(12) United States Patent
Aikawa et al.

(10) Patent No.: US 7,790,447 B2
(45) Date of Patent: Sep. 7, 2010

(54) VECTOR EXPRESSING N-DEACETYLASE/N-SULFOTRANSFERASE 2

(75) Inventors: Jun-ichi Aikawa, Wako (JP); Masafumi Tsujimoto, Wako (JP); Takuji Kaneko, Higashiyamato (JP)

(73) Assignees: Riken, Wako-shi (JP); Seikagaku Corporation, Tokyo (JP)

( * ) Notice: Subject to any disclaimer, the term of this patent is extended or adjusted under 35 U.S.C. 154(b) by 193 days.

(21) Appl. No.: 11/658,762

(22) PCT Filed: Jul. 27, 2005

(86) PCT No.: PCT/JP2005/014160
§ 371 (c)(1),
(2), (4) Date: Jun. 6, 2008

(87) PCT Pub. No.: WO2006/011646
PCT Pub. Date: Feb. 2, 2006

(65) Prior Publication Data
US 2009/0053735 A1    Feb. 26, 2009

(30) Foreign Application Priority Data
Jul. 27, 2004    (JP) .............................. 2004-218598

(51) Int. Cl.
*C12N 15/36* (2006.01)
*C12N 9/00* (2006.01)

(52) U.S. Cl. ..................... 435/320.1; 435/183; 530/530

(58) Field of Classification Search ............... 435/320.1
See application file for complete search history.

(56) References Cited

FOREIGN PATENT DOCUMENTS

JP    2002 325579    11/2002

OTHER PUBLICATIONS

Orellana, et al., "Molecular Cloning and Expression of a Glycosaminoglycan N-acetylglucosaminyl N-Deacetylase/N-Sulfotransferase From a Heparin-Producing Cell Line", Journal of Biological Chemistry, American Society of Biochemical Biologists, vol. 269, No. 3, Jan. 21, 1994, pp. 2270-2276.

Saribas, et al., Production of N-Sulfated Polysaccharides Using Yeast-Expressed N-Deacetylase/N-Sulfotransferase-1 (NDST-1), Glycobiology, vol. 14, No. 12, 2004, pp. 1217-1228.
Grobe, et al., "Regulated Translation of Heparan Sulfate N-Acetylglucosamine N-Deacetylase/N-sulfotransferase Isozymes by Structured 5'-Untranslated Regions and Internal Ribosome Entry Sites", The Journal of Biological Chemistry, vol. 277, No. 34, Aug. 23, 2002, pp. 30699-30706.
Grunwell, et al., Characterization and Mutagenesis of GAL/GLCNAC-6-O-Sulfotransferases, Biochemistry, vol. 41, No. 52, 2002, pp. 15590-15600.
Balagurunathan Kuberan, et al., "Enzymatic Synthesis of Antithrombin III-Binding Heparan Sulfate Pentasaccharide", Nature Biotechnology, vol. 21, No. 11, pp. 1343-1346, 2003.
Jian Liu, et al., "Heparan Sulfate D-Glucosaminyl 3-O-Sulfotransferase-3A Sulfates N-Unsubstituted Glucosamine Residues", The Journal of Biological Chemistry, vol. 274, No. 53, pp. 38155-38162, 1999.
Donald E. Humphries, et al., "cDNA Cloning, Genomic Organization and Chromosomal Localization of Human Heparan Glucosaminyl N-Deacetylase/N-Sulphotransferase-2", Biochem. J., vol. 332, pp. 303-307,1998.
Jun' Ichi Aikawa, "Heparan Ryusan/Heparin No Seigosei Ni Okeru N-Acetyl-Glucosamine. Datsu N-Acetyl Koso/Glucosamine. N-Ryusan Ten' I Koso(N-Deagetylase/N-Sulphotransferase) No Yakuwari", Seikagaku, vol. 73, No. 6, pp. 479-483, 2001.
Cheryl Isaac Murphy, et al., "Enhanced Expression, Secretion , and Large-Scale Purification of Recombinant HIV-1 gp 120 in Insect Cells Using the Baculovirus EGT and p67 Signal Peptides", Protein Expression and Purification, vol. 4, No. 5, pp. 349-357, 1993.
Donald E. Humphries, et al., "Localization of Human Heparan Glucosaminyl N-Deacetylase/N-sulphotransferase to the Trans-Golgi Network", Biochem. J. vol. 325, pp. 351-357, 1997.

*Primary Examiner*—Patrick Nolan
*Assistant Examiner*—Bao Qun Li
(74) *Attorney, Agent, or Firm*—Oblon, Spivak, McClelland, Maier & Neustadt, L.L.P.

(57) ABSTRACT

An object of the present invention is to provide an expression vector that allows for stable production of N-deacetylase/N-sulfotransferase 2 in large amounts and a process for production of N-deacetylase/N-sulfotransferase 2 using the same. The present invention provides a recombinant baculovirus expression vector obtained by incorporating into baculovirus DNA, a DNA fragment having lobster L21 DNA, DNA encoding gp67 signal peptide and DNA encoding the 79th to 883rd amino acids of human N-deacetylase/N-sulfotransferase 2 in this order in the 5' to 3' direction.

9 Claims, 1 Drawing Sheet antihNDST2#1

SEQUENCE LISTING

<160> NUMBER OF SEQ ID NOS: 21

<210> SEQ ID NO 1
<211> LENGTH: 3221
<212> TYPE: DNA
<213> ORGANISM: Homo sapiens

<400> SEQUENCE: 1

```
attcctccct ccttcctcc cccgccatg ctccagttgt ggaaggtggt acgcccagct    60
cggcagctgg aactgcaccg cctcatactg ctgctgatcg ctttcagcct gggctccatg   120
ggcttcctgg cttattatgt gtccaccagc cctaaggcca aggaaccctt gccctgccc   180 ttgggagact gcagcagcgg tggggcagct ggtcctggcc ctgcacggcc tccagttcca   240
cctcggcccc ccaggcctcc agagacagct cgaactgaac ccgtggtcct tgtgtttgtg   300
gagagtgcat actcacagct ggggcaggaa attgtggcca tcctggagtc tagtcgtttt   360
cgttatagca ctgagttggc acctggccga ggggacatgc ccacattgac tgataatacc   420
catggccgct atgtcttggt catttatgag aacctgctca agtatgtcaa cctggatgcc   480
tggagtcggg aactgctaga ccggtactgc gtggagtatg gtgtgggcat cattggcttt   540
ttccgagccc acgagcacag cctactgagc gcccagctca agggctttcc cctttttta   600 cactcaaact tggggctccg ggactaccaa gtgaatcctt ctgccccgct actgcatctc   660
acacgcccca gccgcctaga accagggcca ctgcctggtg atgactggac catcttccaa   720
tccaatcata gtacatatga accagtgctt cttgccagcc ttcggccagc tgagcccgca   780
gtgccaggac cagttcttcg tcgggcccgg cttcccactg tggtacagga cctggggctt   840
catgatggca tccagcgggt gctctttgga catgcctttt ccttctggct ccacaaactt   900
atcttcgttg atgctgttgc ataccctcact ggcaagcgcc tctgcctgga ccttgaccgc   960
tacatcttgg tagacatcga tgacatcttt gtgggcaagg aagggacccg catgaaggtg  1020
gctgatgttg aggctctgtt gaccacccag aacaaactca ggaccttagt tcccaacttc  1080
accttcaact tgggcttctc gggcaagttc tatcatactg ggacagagga ggaggatgca  1140
ggggacgaca tgctgctgaa gcaccgcaaa gagttctggt ggttccccca catgtggagc  1200
cacatgcagc cacacctgtt ccacaatcgc tccgtgctgg ctgaccagat gaggctcaac  1260
aaacagtttg ctctggagca tgggattccc acggacctgg ggtatgctgt ggccccccac  1320 cactcggggtg tgtaccccat ccacacgcag ctctatgagg cctggaaatc cgtgtggggc  1380
atccaggtga ccagcactga ggagtatccc catctccgcc ctgcccgcta ccgccgtggc  1440
ttcattcaca atggcattat ggtgctgccc cggcagacat gtggcctctt cactcacaca  1500
atcttctata atgagtatcc tggaggctct cgtgaactag accggagcat ccgaggtgga  1560
gagctctttc tgacagtgct gcttaatccg atcagcatct ttatgaccca tctgtccaat  1620
tatggaaatg accggctggg cctatacacc tttgagagct tggtgcgctt cctccagtgt  1680
tggacacggc tgcgcctaca gaccttcct cctgtcccac ttgcacagaa gtactttgaa  1740
```

-continued

```
cttttccctc aggagcgaag ccccctttgg cagaatccct gtgatgacaa gaggcacaaa   1800
gatatctggt ccaaggagaa aacctgtgat cgtctcccga agttcctcat tgtgggaccc   1860
cagaaaacag ggactacagc tattcacttc ttcctgagcc tgcacccagc tgtaactagc   1920
agcttcccta gccccagcac atttgaggag attcagttct tcaacagccc taattaccac   1980
aagggtattg actggtacat ggatttcttc cctgttcctt ccaatgccag cactgatttc   2040
ctatttgaaa aaagtgccac ctactttgac tctgaagttg taccacggcg ggggctgcc    2100
ctcctgccac gagccaagat catcacagtg ctcaccaacc tgctgacag gcctactcc     2160
tggtaccagc atcagcgagc ccatggagac ccagttgctc tgaactatac cttctatcag   2220
gtgatttcag cctcctccca gacccctctg gcactacgct ccctgcagaa ccgctgtctt   2280
gtccctggct actattctac ccatctacaa cgctggctga cttactaccc ctctggacag   2340
ttgctgattg tggatgggca agagctgcgt accaacccag cagcctcaat ggagagcatc   2400
cagaagttcc tgggtatcac acccttctg aactacacac ggaccctcag gtttgatgat   2460
gataagggat tttggtgcca gggacttgaa ggtggtaaga ctcgctgtct aggccggagc   2520
aaaggccgga ggtatccaga tatggacact gagtcccgtc ttttccttac ggattttttc   2580
cggaaccata atttggagtt gtcgaagctg ctgagccggc ttggacagcc agtgccctcg   2640
tggcttcggg aagaactgca gcattccagt ctgggctgat gtcccagcct cccataccag   2700
caaaatgccc cctgcttccc taagggtcag gtccagagca gggcccacaa ggggattag    2760
agtggcctgg cccctccccc tctacctcag tagcccccag gctgagatg gctgagaagg    2820
gaagggtatc cttttcccac agttctggga caaataaagg ggcttccttt ggtaccccac   2880
ataatagtgc taggtacctt tgacccatca tcttgggagg tggggaggaa tgagagggtc   2940
caggcagggt gtaggggaat gtattagtcc aatgagattt ccctcttcat ccgcagcagt   3000
gtatctattc tatacctggc tatgggagag accccttgca tgggagggac cccttgctat   3060
ggcccctta gccaggcagt gggatctacc tgtggcccgg cctccctaat gtcattcaca   3120
ttgaatgggg atgaggtcgg acagtggctc atagagccga gtatgagccc tagctgtggg   3180
ctagaaatgt ccttaataaa catccttatt tttcaaaaaa a                       3221
```

<210> SEQ ID NO 2
<211> LENGTH: 883
<212> TYPE: PRT
<213> ORGANISM: Homo sapiens

<400> SEQUENCE: 2

```
Met Leu Gln Leu Trp Lys Val Val Arg Pro Ala Arg Gln Leu Glu Leu
1               5                   10                  15

His Arg Leu Ile Leu Leu Ile Ala Phe Ser Leu Gly Ser Met Gly
            20                  25                  30

Phe Leu Ala Tyr Tyr Val Ser Thr Ser Pro Lys Ala Lys Glu Pro Leu
        35                  40                  45

Pro Leu Pro Leu Gly Asp Cys Ser Ser Gly Ala Ala Gly Pro Gly
    50                  55                  60

Pro Ala Arg Pro Pro Val Pro Pro Arg Pro Arg Pro Glu Thr
65                  70                  75                  80

Ala Arg Thr Glu Pro Val Val Leu Val Phe Val Glu Ser Ala Tyr Ser
                85                  90                  95

Gln Leu Gly Gln Glu Ile Val Ala Ile Leu Glu Ser Ser Arg Phe Arg
            100                 105                 110
```

```
Tyr Ser Thr Glu Leu Ala Pro Gly Arg Gly Asp Met Pro Thr Leu Thr
        115                 120                 125
Asp Asn Thr His Gly Arg Tyr Val Leu Val Ile Tyr Glu Asn Leu Leu
    130                 135                 140
Lys Tyr Val Asn Leu Asp Ala Trp Ser Arg Glu Leu Leu Asp Arg Tyr
145                 150                 155                 160
Cys Val Glu Tyr Gly Val Gly Ile Ile Gly Phe Phe Arg Ala His Glu
                165                 170                 175
His Ser Leu Leu Ser Ala Gln Leu Lys Gly Phe Pro Leu Phe Leu His
            180                 185                 190
Ser Asn Leu Gly Leu Arg Asp Tyr Gln Val Asn Pro Ser Ala Pro Leu
        195                 200                 205
Leu His Leu Thr Arg Pro Ser Arg Leu Glu Pro Gly Pro Leu Pro Gly
    210                 215                 220
Asp Asp Trp Thr Ile Phe Gln Ser Asn His Ser Thr Tyr Glu Pro Val
225                 230                 235                 240
Leu Leu Ala Ser Leu Arg Pro Ala Glu Pro Ala Val Pro Gly Pro Val
                245                 250                 255
Leu Arg Arg Ala Arg Leu Pro Thr Val Val Gln Asp Leu Gly Leu His
            260                 265                 270
Asp Gly Ile Gln Arg Val Leu Phe Gly His Gly Leu Ser Phe Trp Leu
        275                 280                 285
His Lys Leu Ile Phe Val Asp Ala Val Ala Tyr Leu Thr Gly Lys Arg
    290                 295                 300
Leu Cys Leu Asp Leu Asp Arg Tyr Ile Leu Val Asp Ile Asp Asp Ile
305                 310                 315                 320
Phe Val Gly Lys Glu Gly Thr Arg Met Lys Val Ala Asp Val Glu Ala
                325                 330                 335
Leu Leu Thr Thr Gln Asn Lys Leu Arg Thr Leu Val Pro Asn Phe Thr
            340                 345                 350
Phe Asn Leu Gly Phe Ser Gly Lys Phe Tyr His Thr Gly Thr Glu Glu
        355                 360                 365
Glu Asp Ala Gly Asp Asp Met Leu Leu Lys His Arg Lys Glu Phe Trp
    370                 375                 380
Trp Phe Pro His Met Trp Ser His Met Gln Pro His Leu Phe His Asn
385                 390                 395                 400
Arg Ser Val Leu Ala Asp Gln Met Arg Leu Asn Lys Gln Phe Ala Leu
                405                 410                 415
Glu His Gly Ile Pro Thr Asp Leu Gly Tyr Ala Val Ala Pro His His
            420                 425                 430
Ser Gly Val Tyr Pro Ile His Thr Gln Leu Tyr Glu Ala Trp Lys Ser
        435                 440                 445
Val Trp Gly Ile Gln Val Thr Ser Thr Glu Glu Tyr Pro His Leu Arg
    450                 455                 460
Pro Ala Arg Tyr Arg Arg Gly Phe Ile His Asn Gly Ile Met Val Leu
465                 470                 475                 480
Pro Arg Gln Thr Cys Gly Leu Phe Thr His Thr Ile Phe Tyr Asn Glu
                485                 490                 495
Tyr Pro Gly Gly Ser Arg Glu Leu Asp Arg Ser Ile Arg Gly Gly Glu
            500                 505                 510
Leu Phe Leu Thr Val Leu Leu Asn Pro Ile Ser Ile Phe Met Thr His
        515                 520                 525
```

```
Leu Ser Asn Tyr Gly Asn Asp Arg Leu Gly Leu Tyr Thr Phe Glu Ser
    530                 535                 540

Leu Val Arg Phe Leu Gln Cys Trp Thr Arg Leu Arg Leu Gln Thr Leu
545                 550                 555                 560

Pro Pro Val Pro Leu Ala Gln Lys Tyr Phe Glu Leu Phe Pro Gln Glu
                565                 570                 575

Arg Ser Pro Leu Trp Gln Asn Pro Cys Asp Asp Lys Arg His Lys Asp
            580                 585                 590

Ile Trp Ser Lys Glu Lys Thr Cys Asp Arg Leu Pro Lys Phe Leu Ile
        595                 600                 605

Val Gly Pro Gln Lys Thr Gly Thr Thr Ala Ile His Phe Phe Leu Ser
    610                 615                 620

Leu His Pro Ala Val Thr Ser Ser Phe Pro Ser Pro Ser Thr Phe Glu
625                 630                 635                 640

Glu Ile Gln Phe Phe Asn Ser Pro Asn Tyr His Lys Gly Ile Asp Trp
                645                 650                 655

Tyr Met Asp Phe Phe Pro Val Pro Ser Asn Ala Ser Thr Asp Phe Leu
            660                 665                 670

Phe Glu Lys Ser Ala Thr Tyr Phe Asp Ser Glu Val Val Pro Arg Arg
        675                 680                 685

Gly Ala Ala Leu Leu Pro Arg Ala Lys Ile Ile Thr Val Leu Thr Asn
    690                 695                 700

Pro Ala Asp Arg Ala Tyr Ser Trp Tyr Gln His Gln Arg Ala His Gly
705                 710                 715                 720

Asp Pro Val Ala Leu Asn Tyr Thr Phe Tyr Gln Val Ile Ser Ala Ser
                725                 730                 735

Ser Gln Thr Pro Leu Ala Leu Arg Ser Leu Gln Asn Arg Cys Leu Val
            740                 745                 750

Pro Gly Tyr Tyr Ser Thr His Leu Gln Arg Trp Leu Thr Tyr Tyr Pro
        755                 760                 765

Ser Gly Gln Leu Leu Ile Val Asp Gly Gln Glu Leu Arg Thr Asn Pro
    770                 775                 780

Ala Ala Ser Met Glu Ser Ile Gln Lys Phe Leu Gly Ile Thr Pro Phe
785                 790                 795                 800

Leu Asn Tyr Thr Arg Thr Leu Arg Phe Asp Asp Lys Gly Phe Trp
                805                 810                 815

Cys Gln Gly Leu Glu Gly Gly Lys Thr Arg Cys Leu Gly Arg Ser Lys
            820                 825                 830

Gly Arg Arg Tyr Pro Asp Met Asp Thr Glu Ser Arg Leu Phe Leu Thr
        835                 840                 845

Asp Phe Phe Arg Asn His Asn Leu Glu Leu Ser Lys Leu Leu Ser Arg
    850                 855                 860

Leu Gly Gln Pro Val Pro Ser Trp Leu Arg Glu Glu Leu Gln His Ser
865                 870                 875                 880

Ser Leu Gly

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
```
ccatgctcca gttgtggaag gtggtac                                            27

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcattttgct ggtatgggag gctgg                                              25

<210> SEQ ID NO 5
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatcggatcc aactcctaaa aaaccgccac catgctgcta gtaaatcag                    49

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cacgggttca gttcgagctg tctccgcaaa ggcagaatgc gccgc                        45

<210> SEQ ID NO 7
<211> LENGTH: 21
<212> TYPE: DNA
<213> ORGANISM: Homarus sp.

<400> SEQUENCE: 7
aactcctaaa aaaccgccac c                                                  21

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gagacagctc gaactgaacc cgtgg                                              25

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctggtatggc ggccgcaatt gtcagcccag actggaatgc tgcagttc                     48

<210> SEQ ID NO 10

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gatcggatcc aactcctaaa aaaccgccac                                       30

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctggtatggc ggccgcaatt gtcagcccag actggaatgc tgcagttc                   48

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cacgaattcc aaggccaagg aacccttgcc                                       30

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctggtatggc ggccgcaatt gtcagcccag actggaatgc tgcagttc                   48

<210> SEQ ID NO 14
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gaagcagggc ggccgcaatt gctaatggtg atggtgatga tggcccagac tggaatgctg      60
cagttcttc                                                              69

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aactcctaaa aaaccgccac catgaaattc ttagtcaacg ttg                        43
```

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cacgggttca gttcgagctg tctccgcata gatgtaagaa atgtatac                48

<210> SEQ ID NO 17
<211> LENGTH: 13
<212> TYPE: PRT
<213> ORGANISM: Homo sapiens

<400> SEQUENCE: 17

Leu Gly Arg Ser Lys Gly Arg Arg Tyr Pro Asp Met Asp
1               5                   10

<210> SEQ ID NO 18
<211> LENGTH: 11
<212> TYPE: PRT
<213> ORGANISM: Homo sapiens

<400> SEQUENCE: 18

Leu Arg Glu Glu Leu Gln His Ser Ser Leu Gly
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Leu Gly Arg Ser Lys Gly Arg Arg Tyr Pro Asp Met Asp
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Leu Arg Glu Glu Leu Gln His Ser Ser Leu Gly
1               5                   10

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 21

His His His His His His
1               5

VECTOR EXPRESSING N-DEACETYLASE/N-SULFOTRANSFERASE 2

CROSS-REFERENCE TO RELATED APPLICATIONS

The present application is a 35 U.S.C. §371 National Stage patent application of International patent application PCT/JP05/014160, filed on Jul. 27, 2005, which claims priority to Japanese patent application JP 2004-218598, filed on Jul. 27, 2004.

TECHNICAL FIELD

The present invention relates to an expression vector capable of stably expressing N-deacetylase/N-sulfotransferase 2 in large amounts. More particularly, the present invention relates to an expression vector for stably expressing N-deacetylase/N-sulfotransferase 2 in large amounts by using a baculovirus system.

BACKGROUND ART

N-deacetylase/N-sulfotransferase 2 is an enzyme that catalyzes both N-deacetylation and N-sulfation (Wei Z, Swiedler S J, Ishihara M, Orellana A, Hirschberg C B. A single protein catalyzes both N-deacetylation and N-sulfation during the biosynthesis of heparan sulfate. Proc. Natl. Acad. Sci. USA. 90, 3885-3888. (1993); and U.S. Pat. No. 5,541,095). A transient expression system of human N-deacetylase/N-sulfotransferase 3 in monkey COS-7 cells has heretofore been used for the production of N-deacetylase/N-sulfotransferase (Aikawa J, Esko J D. Molecular cloning and expression of a third member of the heparan sulfate/heparin GlcNAc N-deacetylase/N-sulfotransferase family. J. Biol. Chem. 274, 2690-2695. (1999)), and however, was not suitable for obtaining the enzyme with stable quality in large amounts.

On the other hand, a method is known wherein a protein is extracellularly produced with a baculovirus system. For example, expression of Trypanosoma cruzi trans-sialidase in a baculovirus system using a gp67 signal sequence has been described in Marchal I, Cerutti M, Mir A M, Juliant S, Devauchelle G, Cacan R, Verbert A. Expression of a membrane-bound form of Trypanosoma cruzi trans-sialidase in baculovirus-infected insect cells: a potential tool for sialylation of glycoproteins produced in the baculovirus-insect cells system. Glycobiology. 11, 593-603 (2001). Expression of mouse TSH receptor in a baculovirus system using a gp67 signal sequence has been described in Vlase H, Matsuoka N, Graves P N, Magnusson R P, Davies T F. Folding-dependent binding of thyrotropin (TSH) and TSH receptor autoantibodies to the murine TSH receptor ectodomain. Endocrinology. 138, 1658-1666 (1997). Expression of single-chain antibodies in a baculovirus system using a gp67 signal sequence has been described in Kretzschmar T, Aoustin L, Zingel O, Marangi M, Vonach B, Towbin H, Geiser M. High-level expression in insect cells and purification of secreted monomeric single-chain Fv antibodies. J. Immunol. Methods. 195, 93-101 (1996). Expression of interleukin 1-related T1 receptor in a baculovirus system using a gp67 signal sequence has been described in Rupp B, Rossler U, Lowel M, Werenskiold A K. High level expression of the IL-1 receptor related T1 receptor in insect cells. Biochem. Biophys. Res. Commun. 216, 595-601 (1995). Moreover, expression of human AIDS virus envelop protein gp120 in a baculovirus system using a gp67 signal sequence has been described in Murphy C I, McIntire J R, Davis D R, Hodgdon H, Seals J R, Young E. Enhanced expression, secretion, and large-scale purification of recombinant HIV-1 gp120 in insect cell using the baculovirus egt and p67 signal peptides. Protein Expr. Purif. 4, 349-357. (1993). Erratum in: Protein Expr. Purif. 5, 103 (1994).

Moreover, polypeptide expression using a baculovirus-cultured insect cell system has been described in JP Patent Publication (Kokai) No. 2002-325579A (2002) and year Heisei 13, Riken research annual report, 681-687, Structural Biochemistry Laboratory, 4. Construction of Highly Efficient Protein Expression System Using Insect Cells, (1) Expression-Enhancing Factor (Sano and Maeda Y.; and Maeda K. (Cellular Signaling Laboratory)), wherein drastic increase in polypeptide expression level is seen by inserting a lobster-derived nontranslated leader sequence L21 upstream of the coding sequence of the polypeptide.

Furthermore, a case has been introduced recently wherein the amino acids of human N-deacetylase/N-sulfotransferase 2 are expressed in the form of a fusion protein with a His tag in a baculovirus system (Balagurunathan Kuberan, et al., Nature Biotechnology 1 Nov. 2003; 21, 1343-1346).

DISCLOSURE OF THE INVENTION

As described above, expression systems known in the art for transient expression using COS-7 cells could not stably produce N-deacetylase/N-sulfotransferase in large amounts and were not practical. An object to be attained by the present invention is to provide an expression vector that allows for stable production of N-deacetylase/N-sulfotransferase 2 in large amounts and a process for production of N-deacetylase/N-sulfotransferase 2 using the expression vector.

The present inventors have conducted diligent studies for the purpose of producing human N-deacetylase/N-sulfotransferase 2 (also referred to as human NDST2) in large amounts by use of a baculovirus system, and have consequently completed the present invention by finding out that a protein having both N-deacetylase activity and N-sulfotransferase activity can be secreted stably in large amounts into a medium by directly ligating the signal sequence of baculovirus gp67, melittin, bombyxin, or the like to a DNA fragment encoding the 79th and subsequent amino acids of human N-deacetylase/N-sulfotransferase 2.

Specifically, the present invention provides (1) a human N-deacetylase/N-sulfotransferase 2 of the following (a) or (b), wherein the N-terminal sequence of the transmembrane domain has been removed:

(a) a protein comprised of an amino acid sequence at the 79th to 883rd positions of SEQ ID NO: 2; or (b) a protein comprised of an amino acid sequence of the protein (a) with the deletion, substitution, insertion, or transposition of one or several amino acids, and having N-deacetylase activity and N-sulfotransferase activity.

In another aspect, the present invention provides (2) a transfer vector which comprises at least signal peptide-encoding DNA capable of functioning in a baculovirus expression vector and DNA encoding the protein according to (1) which is ligated downstream of the signal peptide-encoding DNA. It is preferred that the signal peptide-encoding DNA capable of functioning in a baculovirus expression vector is DNA encoding a signal peptide derived from a baculovirus, silkworm, or bee. Moreover, it is preferred that the transfer vector further comprises a nontranslated leader sequence having a function of promoting the expression of the coding sequence. It is more preferred that the signal peptide derived from a baculovirus, silkworm, or bee is gp67, a bombyxin signal peptide, or a melittin signal peptide, respectively, and the nontranslated leader sequence is lobster L21 DNA. Moreover, it is preferred that the transfer vector further comprises DNA corresponding to a histidine tag downstream of DNA encoding the protein according to (1).

In a further alternative aspect, the present invention provides (3) a recombinant baculovirus expression vector obtained by incorporating into baculovirus DNA, a DNA fragment having at least DNA encoding a signal peptide derived from a baculovirus and DNA encoding the 79th to 883rd amino acids of human N-deacetylase/N-sulfotransferase 2 or DNA derived from the DNA with deletion, insertion, or substitution of one or several nucleotides and encoding a protein exhibiting enzyme activity equal to that of human N-deacetylase/N-sulfotransferase 2 in this order in the 5' to 3' direction. It is preferred that the incorporation of the DNA fragment into the baculovirus DNA should be performed by homologous recombination between the DNA fragment and a polyhedrin gene of the baculovirus DNA.

In a further alternative aspect, the present invention provides (4) an insect cell which comprises the recombinant baculovirus expression vector of the present invention. The insect cell is preferably a *Spodoptera frugiperda* cell.

In a further alternative aspect, the present invention provides (5) a process of production of human N-deacetylase/N-sulfotransferase 2, which comprises culturing the insect cell comprising the recombinant baculovirus expression vector of the present invention and causing by secretion, the expression of human N-deacetylase/N-sulfotransferase 2 from which the N-terminal sequence of the transmembrane domain has been removed. Preferably, the insect cell is cultured in a serum-containing medium.

In a further alternative aspect, the present invention provides (6) human N-deacetylase/N-sulfotransferase 2 which is comprised of the 79th to 883rd amino acids, which is produced by the production process.

In a further alternative aspect, the present invention provides (7) a method for detecting human N-deacetylase/N-sulfotransferase 2, which comprises the step of reacting the human N-deacetylase/N-sulfotransferase 2 of the above (1) with an antibody capable of immunologically reacting with human N-deacetylase/N-sulfotransferase 2. Preferably, the antibody is a polyclonal antibody or monoclonal antibody which is obtained by immunizing mammals or birds with an antigenic peptide comprising any consecutive 11 to 13 amino acids of SEQ ID NO: 2.

BEST MODE FOR CARRYING OUT THE INVENTION

Figure 1:
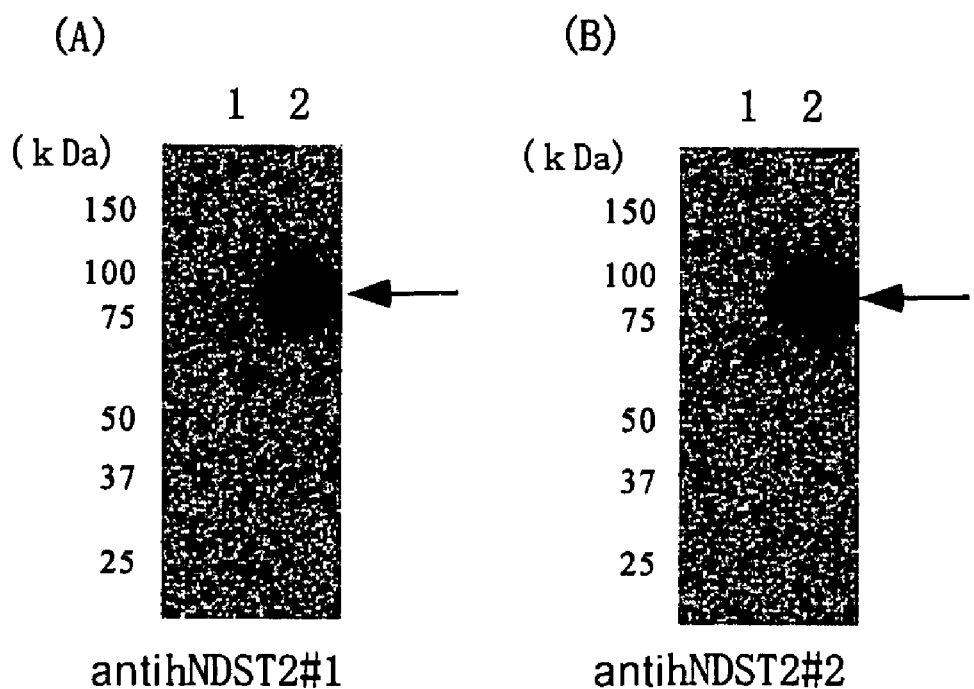
FIG. 1 shows a result of detecting human NDST2 in a *Spodoptera frugiperda* cell by using a purified anti-human NDST2 antibody.

Hereinafter, the embodiments of the present invention will be described in detail.

Human N-deacetylase/N-sulfotransferase 2 of the present invention from which the N-terminal sequence has been removed is characterized in that it is a protein comprising an amino acid sequence at the 79th to 883rd positions of SEQ ID NO: 2 in which the 1st to 78th amino acids serving as the N-terminal sequence of the transmembrane domain have been removed from the amino acid sequence of SEQ ID NO: 2. The truncated human NDST2 comprising an amino acid sequence at the 79th to 883rd positions, which is obtained by the present invention, is the shortest active human NDST2 polypeptide known so far and has the excellent advantages of being soluble and highly active. A protein (such a protein is also referred to as a "mutant protein" or "mutant") having a sequence of the truncated human NDST2 with the deletion, substitution, insertion, or transposition of one or several (preferably 1 to 3, more preferably 1 to 2) amino acids and having N-deacetylase activity and N-sulfotransferase activity can be prepared appropriately according to the description of the present specification by those skilled in the art on the basis of information about the amino acid sequence of SEQ ID NO: 2 and the nucleotide sequence of SEQ ID NO: 1, and therefore, is included in the present invention. The "protein having a sequence of the truncated human NDST2 with the deletion, substitution, insertion, or transposition of one or several amino acids" can be said to be a protein having high homology to the amino acid sequence at the 79th to 883rd positions of SEQ ID NO: 2 and having N-deacelylase activity and N-sulfotransferase activity. In this context, the "high homology" refers to, for example, 75% or higher, preferably 80% or higher, more preferably 90% or higher, even more preferably homology of higher percentage exemplified by 91%, 92%, 93%, 94%, 95%, 96%, 97%, 98%, 99%, 99.5%, and 99.9% in this order. For example, such a protein can be obtained with a method of contacting DNA having the nucleotide sequence of SEQ ID NO: 1 with a mutagenic drug, a method of ultraviolet irradiation of the DNA, a genetic engineering approach, or the like.

A site-specific mutagenesis method, one of the genetic engineering approaches, is useful because it is an approach that can introduce a particular mutation at a particular position. The method can be performed in accordance with methods described in, for example, Molecular Cloning Vol. 2, Current Protocols in Molecular Biology, Nucleic Acids Research, 10, 6487, 1982, Nucleic Acids Research, 12, 9441, 1984, Nucleic Acids Research, 13, 4431, 1985, Nucleic Acids Research, 13, 8749, 1985, Proc. Natl. Acad. Sci. USA, 79, 6409, 1982, Proc. Natl. Acad. Sci. USA, 82, 488, 1985, Gene, 34, 315, 1985, and Gene, 102, 67, 1991. DNA having a nucleotide sequence which is derived from the nucleotide sequence of SEQ ID NO: 1 and has a mutation can be obtained by the aforementioned method, and can be subjected to expression to thereby produce the protein of interest.

A transfer vector of the present invention comprises at least DNA encoding a signal peptide, preferably a signal peptide derived from a baculovirus, silkworm or bee, which is capable of functioning in a baculovirus expression vector, and DNA encoding the human N-deacetylase/N-sulfotransferase 2, which is ligated downstream of the DNA encoding the signal peptide. It is preferred that a nontranslated leader sequence having a function of promoting the expression of coding sequence should be inserted upstream of the signal peptide-encoding DNA in order to enhance translation efficiency and the expression efficiency of the protein of interest. The signal peptide derived from a baculovirus, silkworm, or bee is exemplified by gp67, a bombyxin signal peptide, or a melittin signal peptide, respectively. The nontranslated leader sequence is exemplified by lobster L21 DNA and is preferably the lobster L21 DNA. The signal peptide is most preferably the baculovirus gp67. A production process of such a transfer vector will be described later in detail.

A recombinant baculovirus expression vector of the present invention can be obtained by incorporating into baculovirus DNA, a DNA fragment having at least DNA encoding a signal peptide derived from a baculovirus and DNA encoding the 79th to 883rd amino acids of human N-deacetylase/N-sulfotransferase 2 or DNA derived from the DNA with deletion, insertion, or substitution of one or several nucleotides and encoding a protein exhibiting enzyme activity equal to that of human N-deacetylase/N-sulfotransferase 2 in this order in the 5' to 3' direction.

The recombinant baculovirus expression vector of the present invention is most preferably a baculovirus expression vector in which a lobster L21 sequence (for enhancing translation efficiency), a gp67 signal peptide (for enhancing secretion efficiency), and the amino acid sequence at the 79th to 883rd positions (the smallest region currently known necessary for enzyme activity) of human N-deacetylase/N-sulfotransferase 2 are ligated to each other for the purpose of obtaining the maximum activity and incorporated.

In the present invention, DNA encoding the 79th to 883rd amino acids of human N-deacetylase/N-sulfotransferase 2 is employed. Wild-type human N-deacetylase/N-sulfotransferase 2 as well as a mutant prepared by genetic engineering may be used. Examples of such a mutant include DNA derived from the wild-type DNA sequence with the deletion, insertion, or substitution of one or several (preferably 1 to 10, more preferably 1 to 6, even more preferably approximately 1 to 3) nucleotides by a gene recombination technique well known by those skilled in the art or DNA having homology (e.g., 75% or higher, preferably 90% or higher, more preferably 95% or higher homology) to the wild-type DNA sequence, wherein the DNA encodes a protein having biological activity equal to or higher than that of naturally occurring wild-type human N-deacetylase/N-sulfotransferase 2.

Specific examples of the 79th to 883rd amino acids of human N-deacetylase/N-sulfotransferase 2 include the 79th to 883rd positions of the amino acid sequence of SEQ ID NO: 2. Specific examples of a nucleotide sequence encoding the amino acid sequence of SEQ ID NO: 2 include the nucleotide sequence of SEQ ID NO: 1. These DNA can be cloned by use of a genetic engineering approach known per se in the art or can be produced by use of a commercially available nucleic acid synthesizer.

In the present invention, lobster L21 DNA is used for enhancing translation efficiency. AACTCCTAAAAAAC-CGCCACC (SEQ ID NO: 7) can be used as the lobster L21 DNA.

Signal peptide-encoding DNA is used in the transfer vector and the recombinant baculovirus expression vector of the present invention. The signal sequence is an amino acid sequence necessary for the secretion of extracellular proteins from within a cell to outside the cell. The signal peptide-encoding DNA used in the present invention is ligated with the N-terminus of a secretory protein, and is removed by cleavage during the secretion of the protein to outside the cell. Such signal peptide-encoding DNA is not particularly limited as long as it is DNA capable of functioning in a baculovirus expression vector. Examples thereof include DNAs known in the art, which encode a gp67 signal peptide (signal peptide derived from a baculovirus), a silkworm 30K protein signal peptide (see Sakai et al., 1988: Biochim. Biophys. Acta 949, 224-232; and JP Patent Publication (Kokai) No. 2002-300886A (2002)), bombyxin, and melittin (JP Patent Publication (Kohyo) No. 11-505410A (1999), and U.S. Pat. Nos. 6,582,691 and 6,911,204). The DNA encoding a gp67 signal peptide is preferable.

A baculovirus, a virus infecting insects and causing disease, is an envelope virus having circular double-stranded DNA as a gene, and exhibits sensitivity to insects such as Lepidoptera, Hymenoptera, and Diptera. Among baculoviruses, a group of viruses are nuclear polyhedrosis viruses (NPV), which form large amounts of inclusion bodies called polyhedra within the nuclei of infected cells. The polyhedra are composed of polyhedrin proteins with a molecular weight of 31 kDa, and are produced in large amounts at the late stage of infection, in which a large number of virus particles are embedded. The polyhedra are essential for the survival of the virus in the natural world but is not necessary for virus proliferation itself. Therefore, the virus achieves infection and growth without any trouble even if a foreign gene to be expressed is inserted instead of the polyhedra gene.

For introducing DNA encoding the 79th to 883rd amino acids of human N-deacetylase/N-sulfotransferase 2 into an insect cell and causing the efficient expression thereof, it is preferred that the DNA should be incorporated downstream of the polyhedrin promoter of a nuclear polyhedrosis virus (NPV) or the like belonging to a baculovirus whose host is an insect cell. A virus such as Autographa californica NPV (AcNPV) of the Subfamily Plusiinae and silkworm Bombyx mori NPV (BmNPV) is used as the vector.

As described above, examples of the baculovirus whose host cell is an insect cell include a nuclear polyhedrosis virus (NPV). Examples of the insect cell, for example, for the AcNPV virus, include an armyworm-derived cell line (Spodoptera frugiperda cell; Sf cell), Trichoplusia ni midgut-derived MG-1 cell, Trichoplusia ni egg-derived High Five™ cell, Mamestrabrassicae-derived cell, Estigmena acrea-derived cell, and Drosophila melanogaster-derived cell (e.g., Schneider cells). Among them, particularly, Sf9 and Sf21 cells [Vaughn, J. L. et al., In Vitro, 13, 213-217, (1977)] can be subjected to static culture and suspension culture. Examples of the insect cell for the BmNPV virus include a silkworm-derived cell line (Bombyx mori N; BmN cell) and a silkworm larva individual. Examples of the Sf cell include Sf9 cells (ATCC CRL1711) and Sf21 cells [both: Vaughn, J. L. et al., In Vitro, 13, 213-217, (1977)].

A method comprising adding a baculovirus at m.o.i. (multiplicity of infection) of approximately 0.1 to 100, desirably approximately 1 to 10, to the culture solution of an insect cell is used as a method for infecting an insect cell with a baculovirus.

The recombinant baculovirus expression vector of the present invention may be constructed according to a standard method and can be constructed, for example, by the following procedures: first, a gene to be expressed, that is, DNA encoding the 79th to 883rd amino acids of human N-deacetylase/N-sulfotransferase 2 (preferably, this DNA is ligated with lobster L21 DNA and DNA encoding a gp67, bombyxin, or melittin signal peptide) is inserted into a transfer vector to construct a recombinant transfer vector. The transfer vector is generally several kb to approximately 10 kb in whole size. For example, of the transfer vector, approximately 3 kb is a skeleton derived from a plasmid and may contain an antibiotic (e.g., ampicillin) resistance gene and a signal of bacterial DNA replication initiation. A usual transfer vector contains the 5' region of several kb and 3' region of several kb of a polyhedrin gene in addition to the skeleton. During transfection described below, homologous recombination between the gene of interest and the polyhedrin gene is caused between these sequences. Moreover, it is preferred that the transfer vector should contain a promoter for expressing the gene of the protein. Examples of the promoter include a polyhedrin gene promoter, p10 gene promoter, and capsid gene promoter.

The type of the transfer vector is not particularly limited. Specific examples thereof include: AcNPV transfer vectors such as pEVmXIV2, pAcSGI, pVL1392/1393, pAcMP2/3, pAcJP1, pAcUW21, pAcDZ1, pBlueBacIII, pAcUW51, pAcAB3, pAc360, pBlueBacHis, pVT-Bac33, pAcUW1, pAcUW42/43, and pAcC4; and BMNPV transfer vectors such as pBK283, pBK5, pBB30, pBE1, pBE2, pBK3, pBK52, pBKblue, pBKblue2, and pBF series (all available from Funakoshi Co., Ltd., Fujisawa Pharmaceutical Co., Ltd., etc).

Next, in order to prepare a recombinant virus, the recombinant transfer vector is mixed with a virus and then introduced into a cultured cell used as a host. Alternatively, the transfer vector is introduced into a cultured cell used as a host infected in advance with a virus. As a result, a recombinant virus can be constructed by causing homologous recombination between the recombinant transfer vector and the virus genomic DNA.

Various kits are commercially available for the purpose of protein expression using a baculovirus, and can be used in the present invention. In many systems, cloning is performed by cotransfecting an insect cell with virus genomic DNA and a transfer vector into which a gene to be expressed has been subcloned, and then performing blue/white screening with β-gal. Alternatively, BAC-TO-BAC commercially available from Gibco BRL is a system without need of cloning at an insect cellular level, wherein the recombination of cDNA of a protein of interest into baculovirus DNA is performed in *Escherichia coli*. The 130-kb virus DNA is incorporated in a host *Escherichia coli* DH10BAC, to which a transfer vector pFASTBAC comprising the cDNA of interest inserted therein is introduced in the same way as in usual *Escherichia coli* transformation. As a result, a recombinant can be selected by blue/white screening on the *Escherichia coli*. The recombinant virus DNA can be extracted with usual alkaline miniprep and transfected into a cell. The transfer vector pFASTBAC includes tag-free pFASTBAC1, 6×HIS-tagged (SEQ ID NO: 21) pFASTBAC-HTa, b, and c, and pFASTBAC-DUAL for the coexpression of two proteins. In the present invention, these transfer vectors can be selected appropriately according to the purposes and used.

The protein of the present invention comprising the 79th to 883rd amino acids of human N-deacetylase/N-sulfotransferase 2 can be produced by culturing, under conditions permitting for the expression of DNA encoding the 79th to 883rd amino acids of human N-deacetylase/N-sulfotransferase 2, an insect cell infected with a baculovirus in which DNA encoding the 79th to 883rd amino acids of human N-deacetylase/N-sulfotransferase 2 has been introduced. Specifically, the insect cell infected with the baculovirus comprising the DNA introduced therein can be cultured statically or suspension-cultured to thereby cause the expression into the cell, of large amounts of the protein comprised of the amino acid sequence at the 79th to 883rd positions of human N-deacetylase/N-sulfotransferase 2.

Examples of a medium for culturing the insect cell include a Grace's medium for insect cells containing supplements, IPL-41 medium for insect cells, Sf-900 serum-free medium for insect cells, and TC-100 medium for insect cells (all from GIBCO-BRL). Moreover, these media may be supplemented with approximately 5% to 20% fetal bovine serum, antibiotics such as penicillin G, streptomycin, and gentamycin, approximately 0.1% Pluronic F-68 (GIBCO-BRL), and so on.

The culture can be performed at approximately 20° C. to 30° C., desirably approximately 26° C. to 28° C., for approximately 12 hours to 144 hours, desirably approximately 24 hours to 96 hours. The culture may be performed with standing in a petri dish or flask or with stirring at approximately 50 rpm to 200 rpm by use of a spinner flask.

As described above, an appropriate host (e.g., cultured cells such as *Spodoptera Frugiperda* cell lines Sf9 and Sf21, or infect larvae) is infected with the recombinant baculovirus expression vector of the present invention, and is cultured under suitable conditions to cause the expression of human N-deacetylase/N-sulfotransferase 2 by secretion. After given periods (e.g., after 72 hours), cultures are subjected to centrifugation or the like. As a result, the N-deacetylase/N-sulfotransferase 2 of interest can be obtained by collecting the culture supernatant.

The recombinant N-deacetylase/N-sulfotransferase 2 can be collected and purified from the culture supernatant by appropriately combining separation and purification methods known in the art, if necessary. Specific examples of the separation and purification methods that can be used include: methods using solubility, such as salting-out with ammonium sulfate or the like and a solvent precipitation method; methods mainly using difference in molecular weight, such as dialysis, ultrafiltration, gel filtration, and SDS-polyacrylamide gel electrophoresis methods; methods using difference in electric charge, such as ion-exchange chromatography; methods using specific affinity, such as affinity chromatography; methods using difference in hydrophobicity, such as reverse phase high-performance liquid chromatography; and methods using difference in isoelectric point, such as an isoelectric focusing method.

Furthermore, according to the present invention, human N-deacetylase/N-sulfotransferase 2 can be detected by the step of reacting the human N-deacetylase/N-sulfotransferase 2 of the present invention with an antibody capable of immunologically reacting with human N-deacetylase/N-sulfotransferase 2. Preferably, a polyclonal antibody or monoclonal antibody obtained by immunizing mammals or birds with an antigenic peptide comprising any consecutive 11 to 13 amino acids of SEQ ID NO: 2 can be used as the antibody.

The antibody used in the present invention may be either a polyclonal or monoclonal antibody. These antibodies can be prepared according to a standard method.

The antibody can be obtained, for example, by immunizing mammals with an antigenic peptide comprising any consecutive 11 to 13 amino acids of SEQ ID NO: 2 or with a complex of Keyhole limpet hemocyanin or the like with the antigenic peptide; collecting blood from the mammals; and separating and purifying antibodies from the collected blood. In the present invention, mammals or birds, for example, mice, hamsters, guinea pigs, chickens, rats, rabbits, dogs, goats, sheep, and cattle, can be immunized. An immunization method generally known by those skilled in the art can be used as a method for the immunization, and can be performed, for example, by administering the antigen one or more times.

The antigen administration can be performed by, for example, 2 or 3 dosages at 7- to 30-day, particularly 12- to 16-day intervals. A single dose can be, for example, approximately 0.05 to 2 mg of the antigen as a guideline. An administration route is not particularly limited and can be selected appropriately from hypodermic administration, intradermal administration, intraperitoneal administration, intravenous administration, intramuscular administration, and so on. It is preferred that the antigen should be administered by intravenous, intraperitoneal, or hypodermic injection. Moreover, the antigen can be dissolved for use in an appropriate buffer solution, for example, an appropriate buffer solution containing an adjuvant usually used such as a complete Freund's adjuvant, RAS [MPL (Monophosphoryl Lipid A)+TDM (Synthetic Trehalose Dicorynomycolate)+CWS (Cell Wall Skeleton) adjuvant system], and aluminum hydroxide. Depending on an administration route, conditions, and so on, the adjuvants are not employed. In this context, the adjuvant refers to a substance that nonspecifically enhances immune reaction against an antigen when administered with the antigen.

The immunized mammals or the like are raised for 0.5 to 4 months. Then, a small amount of serum can be sampled from the auricular veins or the like of the mammals or the like and measured for antibody titers. When the antibody titers start to rise, an appropriate number of antigen administrations are practiced according to the situation. For example, 10 μg to 1000 μg of the antigen can be used to perform a booster. One to two months after the final administration, blood can be collected from the immunized mammals by a usual method and subjected to separation and purification by a usual method such as centrifugation, precipitation using ammonium sulfate or polyethylene glycol, or chromatography (e.g., gel filtration chromatography, ion-exchange chromatography, or affinity chromatography) to thereby obtain a polyclonal antibody as polyclonal antiserum. The complement system may be inactivated by treating the antiserum, for example, at 56° C. for 30 minutes.

Monoclonal antibody preparation can be performed by a method known by those skilled in the art, and can be performed by, for example, a method using hybridomas. Monoclonal antibody-producing cell lines are not particularly limited and can be obtained as hybridomas by, for example, cell fusion between antibody-producing cells and myeloma cell lines. The monoclonal antibody-producing hybridomas can be obtained by a cell fusion method as described below.

Splenocytes, lymph node cells, B-lymphocytes, or the like from immunized animals are used as antibody-producing cells. The antigenic peptide comprising any consecutive 11 to 13 amino acids of SEQ ID NO: 2 can be used as an antigen, as in the polyclonal antibody. Mice, rats, and so on are used as the immunized animals, and antigen administration to these animals is performed according to a standard method. For example, the animals are immunized by preparing a suspension or emulsion of an adjuvant such as a complete or incomplete Freund's adjuvant and the antigen (antigenic peptide comprising any consecutive 11 to 13 amino acids of SEQ ID NO: 2) and administering, for example, intravenously, hypodermically, intradermally, or intraperitoneally, this suspension or emulsion to the animals several times. For example, splenocytes can be obtained as antibody-producing cells from the immunized animals and fused with myeloma cells by a method known per se in the art (G. Kohler et al., Nature, 256, 495 (1975)) to thereby prepare hybridomas.

Examples of the myeloma cell lines used in the cell fusion include mouse P3X63Ag8, P3U1, and Sp2/0 strains. To perform the cell fusion, a fusion promoter such as polyethylene glycol or Sendai virus is used, and a hypoxanthine-aminopterin-thymidine (HAT) medium can be employed according to a standard method in hybridoma selection after cell fusion. The hybridomas obtained by cell fusion can be cloned by a limiting dilution method or the like. Furthermore, cell lines producing a monoclonal antibody capable of immunologically reacting with human N-deacetylase/N-sulfotransferase 2 can be obtained by screening using enzyme immunoassay (ELISA) or the like.

The monoclonal antibody of interest may be produced from the hybridomas thus obtained by culturing the hybridomas by a usual cell culture method or ascites formation method and purifying the monoclonal antibody from the culture supernatant or ascites. The purification of the monoclonal antibody from the culture supernatant or ascites can be performed according to a standard method. For example, ammonium sulfate fractionation, gel filtration, ion-exchange chromatography, and affinity chromatography can be used in appropriate combination.

When the antibody is a monoclonal antibody, the globulin type of the monoclonal antibody is not particularly limited. Examples thereof include IgG, IgM, IgA, IgE, and IgD. Alternatively, fragments of the antibodies of various types can also be used. Examples of the antibody fragments include $F(ab')_2$ and Fab' fragments.

In the present invention, human N-deacetylase/N-sulfotransferase 2 can be detected by reacting the human N-deacetylase/N-sulfotransferase 2 of the present invention with the antibody capable of immunologically reacting with human N-deacetylase/N-sulfotransferase 2 and thereby conducting analysis such as an enzyme antibody technique, immunological tissue staining method, immunoblotting, or direct or indirect fluorescent antibody method. These analyses can be conducted by a method well known by those skilled in the art, and the experimental conditions thereof can be selected appropriately by those skilled in the art.

The descriptions of the documents cited herein are incorporated herein by reference.

Hereinafter, the present invention will be described more specifically with reference to Examples. However, the present invention is not intended to be limited to these Examples.

EXAMPLES

Example 1

Cloning of Human NDST2

(Procedures)

The specific amplification of a region from nucleotide Nos. 26 to 2708 of human NDST2 (NCBI/DDBJ/EMBO Registration No. #36001) was performed by PCR (polymerase chain reaction) using 5 μl of a human adult placenta cDNA library (Clontech, U.S.A.), 5 pmol short chain DNA having a sequence 5'-CCATGCTCCAGTTGTGGAAGGTGGTAC-3' (SEQ ID NO: 3), 5 μmol short chain DNA having a sequence 5'-GCATTTTGCTGGTATGGGAGGCTGG-3' (SEQ ID NO: 4), and 2.5 units of PfuTurbo (Stratagene, U.S.A.) in 50 μl of a reaction system in the presence of 20 mM Tris-HCl (pH 8.8), 2 mM $MgSO_4$, 10 mM KCl, 10 mM $(NH_4)_2SO_4$, 0.1% Triton X-100 (registered trademark), 0.1 mg/ml nuclease-free BSA (bovine serum albumin), and 200 μM dNTP (2'-deoxyribonucleoside 5'-triphosphate/dATP, dCTP, dGTP, and dTTP mixed at an equimolar ratio) under conditions of 1 cycle of 94° C. for 1 minute, 30 cycles of 94° C. for 1 minute-55° C. for 1 minute-72° C. for 6 minutes, and 1 cycle of 72° C. for 10 minutes using a thermal cycler. The reaction product was subjected to Tris-Acetate-EDTA (TAE) agarose electrophoresis, and a DNA fragment of 2683 bp in size of interest was excised, then purified with a Geneclean II kit (Qbiogene, U.S.A.), and collected into 10 μl of 10 mM Tris-HCl (pH 7.6) containing 0.1 mM EDTA (pH 8.0) (TE buffer solution). 4 μl of the collected DNA was ligated to 10 ng of plasmid DNA pPCR-Script Amp SK (+) (Stratagene, U.S.A.) in 10 μl of a reaction system according to the protocol of Stratagene. 40 μl of *Escherichia coli* XL10-Gold Kan competent cells (Stratagene, U.S.A.) was transformed with 2 μl of the reaction solution according to a standard method. Colonies of the transformants were selected on an LB medium containing 1.5% agar and 50 μg/ml ampicillin. The obtained *Escherichia coli* colonies were inoculated into 1.5 ml of an LB medium containing 50 μg/ml ampicillin and shake-cultured at 37° C. for 20 hours. After the centrifugation of the obtained culture solution, plasmid DNA carried by *Escherichia coli* was collected into 100 μl of 10 mM Tris-HCl (pH 8.5) from the *Escherichia coli* cells by use of QIAprep Spin Miniprep Kit (Qiagen, U.S.A.). The nucleotide sequence of the DNA fragment inserted into the vector DNA was confirmed with short chain DNA specific to human NDST2 according to a standard method.

(Results)

As described above, the DNA fragment of 2683 bp in size obtained as a result of the specific amplification of the region from nucleotide Nos. 26 to 2708 of human NDST2 was ligated to pPCR-Script Amp SK (+), with which *Escherichia coli* was then transformed, followed by drug-resistant colony selection. Plasmid DNA was collected from 12 of the obtained *Escherichia coli* colonies, and clones pCRhNDST2#5 and pCRhNDST2#7 carrying the 2683-bp fragment of interest were identified. The nucleotide sequence of the DNA fragment inserted into the vector DNA was analyzed with short chain DNA specific to human NDST2 according to a standard method and confirmed to be completely identical to the nucleotide sequence of registered human NDST2 (NCBI/DDBJ/EMBO Registration No. #36001).

Example 2

Preparation of DNA of Lobster L21 Sequence and gp67 Signal Peptide

The specific amplification of a lobster L21 sequence (AACTCCTAAAAAACCGCCACC) (SEQ ID NO: 7) and DNA encoding 38 amino acids of a gp67 signal peptide was performed by PCR using 250 ng of template vector DNA pAcSecG2T (Pharmingen, U.S.A.) carrying a baculovirus gp67 signal peptide, 5 pmol short chain DNA having a sequence 5'-GATCGGATCCAACTCCTAAAAAACCGC-CACCATGCTGCTAGTAAATCAG-3' (SEQ ID NO: 5), 5 pmol short chain DNA having a sequence 5'-CACGGGT-TCAGTTCGAGCTGTCTCCGCAAAGGCA-GAATGCGCCGC-3' (SEQ ID NO: 6), and 1.25 units of Pyrobest (Takara, Japan) in 25 μl of a reaction system in the presence of 20 mM Tris-HCl (pH 8.3), 10 mM KCl, 6 mM $(NH_4)_2SO_4$, 2 mM $MgSO_4$, 0.1% Triton X-100, 0.001% BSA, and 200 μM dNTP under conditions of 1 cycle of 95° C. for 2 minutes, 10 cycles of 95° C. for 30 seconds-52.5° C. for 30 seconds-72° C. for 1 minute, and 1 cycle of 72° C. for 10 minutes using a thermal cycler.

Example 3

Preparation of DNA Encoding 79th to 883rd Amino Acids of Human NDST2

The specific amplification of DNA encoding 805 amino acids (at the 79th to 883rd positions) of human NDST2 was performed by PCR using 250 ng of template plasmid DNA pCRhNDST2#5 carrying human NDST2 in a vector, 5 pmol short chain DNA having a sequence 5'-GAGACAGCTC-GAACTGAACCCGTGG-3' (SEQ ID NO: 8), 5 pmol short chain DNA having a sequence 5'-CTGGTATGGCGGCCG-CAATTGTCAGCCCAGACTGGAATGCTGCAGTTC-3' (SEQ ID NO: 9), and 1.25 units of Pyrobest (Takara, Japan) in 25 μl of a reaction system in the presence of 20 mM Tris-HCl (pH 8.3), 10 mM KCl, 6 mM $(N)_2SO_4$, 2 mM $MgSO_4$, 0.1% Triton X-100, 0.001% BSA, and 200 μM dNTP under conditions of 1 cycle of 95° C. for 2 minutes, 20 cycles of 95° C. for 30 seconds-52.5° C. for 30 seconds-72° C. for 5 minutes, and 1 cycle of 72° C. for 10 minutes using a thermal cycler.

Example 4

Preparation of Fusion DNA of Lobster L21 Sequence, gp67 Signal Peptide, and Human NDST2

The specific amplification of fusion DNA encoding the lobster L21 sequence, 38 amino acids of the gp67 signal peptide, and 805 amino acids of human NDST2 was performed by PCR using template DNAs in 2 μl of the reaction solution obtained in Example 2 and 0.5 μl of the reaction solution obtained in Example 3, 5 μmol short chain DNA having a sequence 5'-GATCGGATCCAACTC-CTAAAAAACCGCCAC-3' (SEQ ID NO: 10), 5 pmol short chain DNA having a sequence 5'-CTGGTATGGCGGCCG-CAATTGTCAGCCCAGACTGGAATGCTGCAGTTC-3' (SEQ ID NO: 11), and 1.25 units of Pyrobest (Takara, Japan) in 25 μl of a reaction system in the presence of 20 mM Tris-HCl (pH 8.3), 10 mM KCl, 6 mM $(NH_4)_2SO_4$, 2 mM $MgSO_4$, 0.1% Triton X-100, 0.001% BSA, and 200 μM dNTP under conditions of 1 cycle of 95° C. for 2 minutes, 30 cycles of 95° C. for 30 seconds-52.5° C. for 30 seconds-72° C. for 6 minutes, and 1 cycle of 72° C. for 10 minutes using a thermal cycler.

Example 5

Incorporation of Fusion DNA of Lobster L21 Sequence, gp67 Signal Peptide, and Human NDST2 into Vector DNA (Procedures)

10 units each of restriction enzymes BamHI and NotI were added to 10 μl of the reaction solution containing the fusion DNA obtained in Example 4 and 1 μg of vector DNA pFast-Bac-1 (Invitrogen, U.S.A.), and reacted at 37° C. for 2 hours. The reaction products were subjected to TAE agarose electrophoresis according to the method shown in Example 1, and DNA fragments with a size of interest were purified with a Geneclean II kit and collected into 10 μl of a TE buffer solution. In 10 μl of a reaction system using 1 μl each of the obtained DNAs and DNA Ligation Kit ver. 2 (Takara, Japan) at 4° C. for 20 hours, the BamHI/NotI-codigested fusion DNA encoding the lobster L21 sequence, 38 amino acids of the gp67 signal peptide, and 805 amino acids of human NDST2 was ligated to the pFastBac-1 codigested with BamHI and NotI. 40 μl of *Escherichia coli* DH5α competent cells (Invitrogen, U.S.A.) was transformed with 2 μl of the reaction solution according to a standard method. Colonies of the transformants were selected on an LB medium containing 1.5% agar and 50 μg/ml ampicillin. Plasmid DNA carried by *Escherichia coli* was collected into 100 μl of 10 mM Tris-HCl (pH 8.5) from the obtained *Escherichia coli* colonies according to the method shown in Example 1. The nucleotide sequence of the DNA fragment inserted into the vector DNA was analyzed with short chain DNA specific to human NDST2 according to a standard method.

(Results)

2 Clones (pFB1-GP67hNDST2SOL(79E)#5 and pFB1-GP67hNDST2SOL(79E)#123) probably carrying the DNA fragment of interest were identified from 128 clones of *Escherichia coli* transformed with the ligation product of the pFastBac-1 digested with BamHI and NotI and the BamHI/

NotI-digested 2577-bp fragment of the fusion DNA encoding the lobster L21 sequence, 38 amino acids of the gp67 signal peptide, and 805 amino acids of human NDST2. These two clones were confirmed by DNA sequencing to have a nucleotide sequence completely identical to the predicted nucleotide sequence of the DNA.

Example 6

Incorporation of Fusion DNA of Lobster L21 Sequence, gp67 Signal Peptide, and Human NDST2 into Baculovirus Genomic DNA (Procedures)

The DNA obtained in Example 5 was introduced into *Escherichia coli* DH10BAC (Invitrogen, U.S.A.). Colonies of the transformants were selected on an LB medium containing 1.5% agar, 50 μg/ml kanamycin, 7 μg/ml gentamycin, and 10 μg/ml tetracycline according to the protocol of Invitrogen.

The obtained *Escherichia coli* colonies were inoculated into 1.5 ml of a Terrific-Broth medium (Becton Dickinson, U.S.A.) containing 50 μg/ml kanamycin and shake-cultured at 37° C. for 20 hours. The obtained culture solution was transferred to an Eppendorf tube of 1.5 ml. After centrifugation at 8000 rpm at 4° C. for 2 minutes with a cooling centrifuge, the *Escherichia coli* cells were collected as a precipitate. The bacterial cells were suspended in 150 μl of 50 mM Tris-HCl (pH 8.0) containing 10 mM EDTA and 100 μg/ml RNaseA, then added with 150 μl of 200 mM NaOH containing 1% (w/v) SDS (sodium dodecyl sulfate), and gently mixed. The mixture was left standing at room temperature for 5 minutes. Next, 150 μl of 3.0 M potassium acetate (pH 5.5) was added thereto and well mixed. After centrifugation at 15000 rpm at 4° C. for 10 minutes with a cooling centrifuge, the supernatant fraction was collected. 450 μl of phenol saturated in advance with a TE buffer solution (Invitrogen, U.S.A.) was added to 450 μl of the supernatant and vigorously mixed with a vortex mixer. After centrifugation at 15000 rpm at 4° C. for 5 minutes with a cooling centrifuge, the upper-layer fraction was collected. 1 ml of ethanol was added to 400 μl of the upper-layer fraction and mixed. Then, the mixture was left standing at room temperature for 10 minutes. After centrifugation at 15000 rpm at 4° C. for 5 minutes with a cooling centrifuge, the supernatant was removed, and the precipitate was then added with 1 ml of 70% (v/v) ethanol and mixed. After centrifugation at 15000 rpm at 4° C. for 5 minutes with a cooling centrifuge, the supernatant was removed. The remaining precipitate was suspended by the addition of 150 μl of 50 mM Tris-HCl (pH 8.0) containing 10 mM EDTA and 100 μg/ml RNaseA and then reacted at 37° C. for 20 minutes. Next, 100 μl of phenol saturated in advance with a TE buffer (Invitrogen, U.S.A.) solution was added thereto and vigorously mixed with a vortex mixer. After centrifugation at 15000 rpm at 4° C. for 5 minutes with a cooling centrifuge, the upper-layer fraction was collected. 250 μl of ethanol and 10 μl of 3 M sodium acetate (pH 5.2) were added to 100 μl of the upper-layer fraction and mixed. After centrifugation at 15000 rpm at 4° C. for 5 minutes with a cooling centrifuge, the supernatant was removed. Next, the precipitate was added with 1 ml of 70% (v/v) ethanol and mixed. After centrifugation at 15000 rpm at 4° C. for 5 minutes with a cooling centrifuge, the supernatant was removed. The remaining precipitate was suspended by the addition of 100 μl of a TE buffer solution.

(Results)

The DNA pFB1-GP67hNDST2SOL(79E)#123 obtained in Example 5 was introduced into *Escherichia coli* DH10BAC, and a clone of interest (pFB1-GP67hNDST2SOL(79E)#123-4) was obtained with drug resistance and PCR as indexes.

Example 7

Introduction into *Spodoptera frugiperda* Cell, of Baculovirus Genomic DNA Incorporating Therein Fusion DNA of Lobster L21 Sequence, gp67 Signal Peptide, and Human NDST2

First, a million *Spodoptera frugiperda* Sf9 cells were suspended in 2 ml of an SF-900 II serum-free medium (Invitrogen, U.S.A.), then transferred to 6-well plate, and left standing at 28° C. for 1 hour to thereby allow the cells to adhere to the plate. Next, 10 μg of the DNA (baculovirus genomic DNA incorporating therein the lobster L21 sequence, gp67 signal peptide, and human NDST2) obtained in Example 6 was diluted with 100 μl of an Sf-90011 serum-free medium and mixed with 6 μl of cellfectin (Invitrogen, U.S.A.) diluted with 100 μl of an Sf-900 μl serum-free medium. The mixture was left standing at room temperature for 30 minutes. The Sf9 cells allowed in advance to adhere to the plate were washed with 2 ml of an Sf-900 μl serum-free medium and then added with a mixture of 200 μl of the DNA/cellfectin mixture solution and 800 μl of an Sf-90011 serum-free medium. The mixture was left standing at 28° C. for 5 hours. After the removal of the medium by aspiration, 2 ml of a fresh Sf-900 μl serum-free medium was added thereto, and the cells were further cultured at 28° C. for 3 days. Then, the culture supernatant was collected and used as a baculovirus stock solution.

Example 8

Amplification of Virus

Ten million Sf9 cells were suspended in 10 ml of an SF-900 II serum-free medium, then seeded onto a T-75 flask, and left standing for 1 hour. After the removal of the medium except for the 2 ml aliquot thereof by aspiration, 1 ml of the baculovirus stock solution obtained in Example 7 was added thereto and gently shaken for 1 hour. Then, 8 ml of an SF-900 II serum-free medium was added thereto, and the cells were cultured at 28° C. for 3 days. After the centrifugation of the collected medium, the fraction from which the cells were removed was used as a virus amplification solution.

Example 9

Expression of Human NDST2 in *Spodoptera frugiperda* Cell by Secretion

Ten million Sf9 or Sf21 cells were suspended in 10 ml of an SF-900 II serum-free medium or Grace Insect Medium (Invitrogen) containing 10% serum, then seeded onto a T-75 flask, and left standing for 1 hour. After the removal of the medium except for the 2 ml aliquot thereof (or the whole medium) by aspiration, 1 ml of the baculovirus stock solution obtained in Example 7 or 1 ml (or 3 ml) of the virus amplification solution obtained in Example 8 was added thereto and gently shaken for 1 hour. Then, 8 ml of an SF-900 II serum-free medium or Grace Insect Medium (Invitrogen) supplemented with 10% serum was added thereto, and the cells were cultured at 28° C. for 3 days.

Example 10

Condensation of Culture Supernatant

After centrifugation of the collected medium, the fraction from which the cells were removed was used as a culture supernatant. The culture supernatant was applied to Amicon Ultra-15 30000MWCO (Millipore, U.S.A.). A fraction with a molecular weight of 30,000 or higher was collected by centrifugation with a cooling centrifuge and used as a condensed culture supernatant.

More specifically, Sf9 (serum-free medium), Sf9 (serum-containing medium), and Sf21 (serum-containing medium) were infected with the virus stock solution, and the culture supernatants obtained after infection were condensed 20.4-fold, 20.0-fold, and 16.4-fold with Amicon Ultra-15 30000MWCO. Moreover, each cell was infected with a virus stock solution derived from pFastBac-1 carrying no DNA fragment insert, and the culture supernatants condensed 15.2-fold, 21.7-fold, and 16.7-fold were obtained as controls.

Comparative Example 1

Incorporation of Human NDST2 into Protein A-Containing Vector

DNA encoding 841 amino acids (at the 43rd to 883rd positions) of human NDST2 was prepared by PCR using 250 ng of template plasmid DNA pCRhNDST2#5 carrying human NDST2 in a vector, 5 μmol short chain DNA having a sequence 5'-CACGAATTCCAAGGCCAAGGAACCCT-TGCC-3' (SEQ ID NO: 12), 5 μmol short chain DNA having a sequence 5'-CTGGTATGGCGGCCGCAATTGTCAGC-CCAGACTGGAATGCTGCAGTTC-3' (SEQ ID NO: 13), and 1.25 units of Pyrobest (Takara, Japan) in 25 μl of a reaction system in the presence of 20 mM Tris-HCl (pH 8.3), 10 mM KCl, 6 mM $(N)_2SO_4$, 2 mM $MgSO_4$, 0.1% Triton X-100, 0.001% BSA, and 200 μM dNTP under conditions of 1 cycle of 95° C. for 2 minutes, 25 cycles of 95° C. for 30 seconds-52.5° C. for 30 seconds-72° C. for 5 minutes, and 1 cycle of 72° C. for 10 minutes using a thermal cycler. 10 units each of restriction enzymes EcoRI and MunI were added to 10 μl of the reaction solution containing the obtained DNA and reacted at 37° C. for 2 hours. Moreover, 10 units of a restriction enzyme EcoRI were added to 1 μg of vector DNA pRK5F10PROTA and reacted at 37° C. for 2 hours. Then, the vector DNA was subjected to dephosphorylation reaction at 37° C. for 30 minutes by the addition of 1.4 units of bovine intestine-derived Alkaline-phosphatase. The reaction products were subjected to TAE agarose electrophoresis according to the method shown in Example 1, and DNA fragments with a size of interest were purified with a Geneclean II kit and collected into 10 μl of a TE buffer solution. 1 μl each of the obtained DNAs and DNA Ligation Kit ver. 2 (Takara, Japan) were used to insert, at 4° C. for 20 hours, the EcoRI/MunI-codigested DNA encoding 841 amino acids (at the 43rd to 883rd positions) of human NDST2 into the pRK5F10PROTA digested with EcoRI and then dephosphorylated. *Escherichia coli* DH5a competent cells (Invitrogen, U.S.A.) were transformed with the reaction product according to a standard method. After the selection of ampicillin-resistant colonies, a plasmid solution was collected from the *Escherichia coli* cells obtained by shake culture. The nucleotide sequence of the DNA fragment inserted into the vector DNA was analyzed with short chain DNA specific to human NDST2 according to a standard method.

Comparative Example 2

Expression of Human NDST2 in Monkey COS-7 Cell by Secretion

A million monkey COS-7 cells were suspended in 12 ml of a DMEM (high-glucose) medium containing 10% inactivated fetal bovine serum, 0.1 mg/ml streptomycin, and 20 units/ml penicillin (serum-containing DMEM medium), then transferred to a 10-cm culture dish, and cultured at 37° C. for 24 hours in the presence of 5% $CO_2$.

Next, 4 μg of the DNA obtained in Comparative Example 1 was diluted with 300 μl of a DMEM (high-glucose) medium and mixed with 25 μl of Polyfect (Qiagen, U.S.A.). The mixture was left standing at room temperature for 10 minutes. The COS-7 cells were washed with 12 ml of PBS (phosphate-buffered saline) (Nihon Pharmaceutical Co., Ltd., Japan) to remove unnecessary substances and then added with a mixture of 325 μl of the DNA/Polyfect mixture solution and 11 ml of a serum-containing DMEM medium. The mixture was cultured at 37° C. for 72 hours in the presence of 5% $CO_2$. After the completion of the culture, the culture solution was transferred to a 15-ml polypropylene conical tube 35-2196 (Becton Dickinson, U.S.A.) and then centrifuged at 9500 rpm for 10 minutes with a cooling centrifuge. Then, 10 ml of the culture solution was transferred to a fresh 15-ml conical tube. To the tube, 100 μl of IgG-Sepharose (Amersham-Biosciences, Sweden) was added and stirred by rotation at 4° C. for 16 hours with a small rotating stirrer RT-5 (TAITEC, Japan). After the completion of the stirring, centrifugation was performed at 2400 rpm for 5 minutes with a cooling centrifuge, and the supernatant was then removed with a pipette. To the precipitated IgG-Sepharose, 10 ml of 50 mM Tris-HCl (pH 7.4) containing 20% glycerol was added and stirred by rotation at 4° C. for 5 minutes with a small rotating stirrer. After the completion of the stirring, centrifugation was performed at 2400 rpm for 5 minutes with a cooling centrifuge, and the supernatant was then removed with a pipette. To the precipitate, 10 ml of 50 mM Tris-HCl (pH 7.4) containing 20% glycerol was added and stirred by rotation at 4° C. for 5 minutes with a small rotating stirrer.

After the completion of the stirring, centrifugation was performed at 2400 rpm for 5 minutes with a cooling centrifuge, and the supernatant was then removed with a pipette. Finally, the IgG-Sepharose was suspended in 100 μl of 50 mM Tris-HCl (pH 7.4) containing 20% glycerol.

Example 10

Measurement of Enzyme Activity

The enzyme activities of the condensed culture supernatant obtained in Example 9 and the IgG-Sepharose suspension obtained in Comparative Example 2 were detected by methods described below.

N-deacetylase activity: 10 μl of the condensed culture supernatant or 10 μl of the IgG-Sepharose suspension was reacted at 37° C. for 1 hour with tritiated N-acetylheparosan (260000 cpm) and prepared in advance in 50 μl of a reaction system in the presence of 50 mM MES (2-morpholinoethane-sulfonic acid) (pH 6.5), 10 mM $MnCl_2$ and 1% Triton X-100. The reaction was terminated by the addition of a mixture solution of 25 μl of 0.2 N hydrochloric acid, 50 μl of 0.1 N acetic acid, and 50 µl of water. Then, extraction using 250 µl of ethyl acetate was performed three times to collect the reaction product "tritium" acetate.

N-sulfotransferase activity: 10 µl of the condensed culture supernatant or 10 µl of the IgG-Sepharose suspension was reacted at 37° C. for 1 hour with 25 µg of N-desulfated heparin (Sigma, U.S.A.) and 2.5 nmol $^{35}$S-pApS (3'-phosphoadenylyl sulfate) (110000 cpm) in 50l of a reaction system in the presence of 50 mM HEPES (N-2-hydroxyethylpiperazine-N'-2-ethanesulfonic acid) (pH 7.2), 10 mM MgCl$_2$, 1 mM MnCl$_2$, and 1% Triton X-100. The reaction was terminated by the addition of 950 µl of 100 mM EDTA. Next, the sample was applied to 0.5 ml (bed volume) of DEAE-Sepharose (Amersham-Biosciences, Sweden) loaded onto a column and then equilibrated in advance with 2.5 ml of 20 mM sodium acetate (pH 6.0) containing 250 mM sodium chloride. The column was washed with 14 ml of 20 mM sodium acetate (pH 6.0) containing 250 mM sodium chloride, and the heparin to which $^{35}$S-sulfate was transferred was then eluted with 2 ml of 20 mM sodium acetate (pH 6.0) containing 1 M sodium chloride.

Enzyme activity was detected by the methods described above. The activity of a virus-derived culture supernatant derived from pFastBac-1 was subtracted therefrom as a control to calculate activity per ml of the culture supernatant. The results are shown in Table 1 below. The results shown in Table 1 demonstrated that the enzyme of interest can be produced in large amounts by using the expression system of the present invention.

TABLE 1

Detection of enzyme activity

|  | N-deacetylase activity cpm/ml (culture supernatant) |
|---|---|
| COS7 (serum-containing medium) | 1060 |
| Sf9 (serum-free medium) | 5300 |
| Sf9 (serum-containing medium) | 31000 |
| Sf21 (serum-containing medium) | 240000 |
|  | N-sulfotransferase activity pmol/min/ml (culture supernatant) |
| COS7 (serum-containing medium) | 5.99 |
| Sf9 (serum-free medium) | 25.6 |
| Sf9 (serum-containing medium) | 13.0 |
| Sf21 (serum-containing medium) | 120 |

Example 11

Preparation of C-Terminally 6×HIS-Tagged (SEQ ID NO: 21) DNA Encoding 79th to 883rd Amino Acids of Human NDST2

The specific amplification of DNA encoding 805 amino acids (at the 79th to 883rd positions) of human NDST2 was performed by PCR using 250 ng of template plasmid DNA pCRhNDST2#5 carrying human NDST2 in a vector, 5 µmol short chain DNA having a sequence 5'-GAGACAGCTC-GAACTGAACCCGTGG-3' (SEQ ID NO: 8), 5 µmol short chain DNA having a sequence 5'-GAAGCAGGGCGGCCG-CAATTGCTAATGGTGATGGTGATGATG-GCCCAGACTGG AATGCTGCAGTTCTTC-3' (SEQ ID NO: 14), and 1.25 units of Pyrobest (Takara, Japan) in 25 µl of a reaction system in the presence of 20 mM Tris-HCl (pH 8.3), 10 mM KCl, 6 mM (NH$_4$)$_2$SO$_4$, 2 mM MgSO$_4$, 0.1% Triton X-100, 0.001% BSA, and 200 µM dNTP under conditions of 1 cycle of 95° C. for 2 minutes, 20 cycles of 95° C. for 30 seconds-52.5° C. for 30 seconds-72° C. for 5 minutes, and 1 cycle of 72° C. for 10 minutes using a thermal cycler.

Example 12

Preparation of Fusion DNA of Lobster L21 Sequence, gp67 Signal Peptide, and C-Terminally 6×HIS Tagged (SEQ ID NO: 21) Human NDST2

The specific amplification of fusion DNA encoding the lobster L21 sequence, 38 amino acids of the gp67 signal peptide, and 805 amino acids of the C-terminally 6×HIS tagged (SEQ ID NO: 21) human NDST2 was performed by PCR using template DNAs in 2 ul of the reaction solution obtained in Example 3 and 0.5 µl of the reaction solution obtained in Example 11, 5 pmol short chain DNA having a sequence 5'-GATCGGATCCAACTCCTAAAAAACCGC-CAC-3' (SEQ ID NO: 10), 5 pmol short chain DNA having a sequence 5'-GAAGCAGGGCGGCCGCAATTGCTAATG-GTGATGGTGATGATGGCCCAGACTGGA ATGCTG-CAGTTCTTC-3' (SEQ ID NO: 14), and 1.25 units of Pyrobest (Takara, Japan) in 25 µl of a reaction system in the presence of 20 mM Tris-HCl (pH 8.3), 10 mM KCl, 6 mM (NH$_4$)$_2$SO$_4$, 2 mM MgSO$_4$, 0.1% Triton X-100, 0.001% BSA, and 200 µM dNTP under conditions of 1 cycle of 95° C. for 2 minutes, 30 cycles of 95° C. for 30 seconds-52.5° C. for 30 seconds-72° C. for 6 minutes, and 1 cycle of 72° C. for 10 minutes using a thermal cycler.

Example 13

Incorporation of Fusion DNA of Lobster L21 Sequence, gp67 Signal Peptide, and C-Terminally 6×HIS Tagged (SEQ ID NO: 21) Human NDST2 into Vector DNA (Procedures)

10 units each of restriction enzymes BamHI and NotI were added to 10 µl of the reaction solution containing the fusion DNA obtained in Example 12 and 1 µg of vector DNA pFast-Bac-1 (Invitrogen, U.S.A.) and reacted at 37° C. for 2 hours. The reaction products were subjected to TAE agarose electrophoresis according to the method shown in Example 1, and DNA fragments with a size of interest were purified with a Geneclean II kit and collected into 10 µl of a TE buffer solution. In 10 µl of a reaction system using 1 µl each of the obtained DNAs and DNA Ligation Kit ver. 2 (Takara, Japan) at 4° C. for 20 hours, the BamHI/NotI-codigested fusion DNA encoding the lobster L21 sequence, 38 amino acids of the gp67 signal peptide, and 805 amino acids of the C-terminally 6×HIS tagged (SEQ ID NO: 21) human NDST2 was ligated to the pFastBac-1 codigested with BamHI and NotI. 40 µl of *Escherichia coli* DH5α competent cells (Invitrogen, U.S.A.) was transformed with 2 µl of the reaction solution according to a standard method. Colonies of the transformants were selected on an LB medium containing 1.5% agar and 50 µg/ml ampicillin. Plasmid DNA carried by *Escherichia coli* was collected into 100 µl of 10 mM Tris-HCl (pH 8.5) from the obtained *Escherichia coli* colonies according to the method shown in Example 1. The nucleotide sequence of the DNA fragment inserted into the vector DNA was analyzed with short chain DNA specific to human NDST2 according to a standard method.

(Results)

A clone probably carrying the DNA fragment of interest was identified from *Escherichia coli* transformed with the ligation product. The nucleotide sequence of the DNA thereof was confirmed.

Example 14

Incorporation of Fusion DNA of Lobster L21 Sequence, gp67 Signal Peptide, and C-Terminally 6×HIS Tagged (SEQ ID NO: 21) Human NDST2 into Baculovirus Genomic DNA (Procedures)

The DNA obtained in Example 13 was introduced into *Escherichia coli* DH10BAC (Invitrogen, U.S.A.), and DNA was collected by the method shown in Example 6.

(Results)

A clone of interest (pGP67sp-hNDST2(79E)123HIS-FB1/10B#2) was obtained from the DNA obtained in Example 13.

Example 15

Introduction into *Spodoptera frugiperda* Cell, of Baculovirus Genomic DNA Incorporating Therein Fusion DNA of Lobster L21 Sequence, gp67 Signal Peptide, and C-Terminally 6×HIS Tagged (SEQ ID NO: 21) Human NDST2

The DNA (baculovirus genomic DNA incorporating therein the lobster L21 sequence, gp67 signal peptide, and C-terminally 6×HIS tagged (SEQ ID NO: 21) human NDST2) obtained in Example 14 was used to prepare a baculovirus stock solution according to the method shown in Example 7.

Example 16

Preparation of DNA of Lobster L21 Sequence and Bee Melittin Signal Peptide

The specific amplification of DNA encoding a lobster L21 sequence (AACTCCTAAAAAACCGCCACC) (SEQ ID NO: 7) and 21 amino acids of a melittin signal peptide was performed by PCR using 250 ng of template vector DNA pMelBac-A (Invitrogen, U.S.A.) carrying a bee melittin signal peptide, 5 pmol short chain DNA having a sequence 5'-AACTCCTAAAAAACCGCCACCATGAAAT-TCTTAGTCAACGTTG-3' (SEQ ID NO: 15), 5 pmol short chain DNA having a sequence 5'-CACGGGTTCAGTTC-GAGCTGTCTCCGCATAGATGTAAGAAATGTATAC-3' (SEQ ID NO: 16), and 1.25 units of Pyrobest (Takara, Japan) in 25 μl of a reaction system in the presence of 20 mM Tris-HCl (pH 8.3), 10 mM KCl, 6 mM (NH₄)₂SO₄, 2 mM MgSO₄, 0.1% Triton X-100, 0.001% BSA (bovine serum albumin), and 200 μM dNTP under conditions of 1 cycle of 95° C. for 2 minutes, 10 cycles of 95° C. for 30 seconds-52.5° C. for 30 seconds-72° C. for 1 minute, and 1 cycle of 72° C. for 10 minutes using a thermal cycler.

Example 17

Preparation of Fusion DNA of Lobster L21 Sequence, Melittin Signal Peptide, and Human NDST2

The specific amplification of fusion DNA encoding the lobster L21 sequence, 21 amino acids of the melittin signal peptide, and 805 amino acids of human NDST2 was performed by the method shown in Example 4 using the template DNAs in 2 ul of the reaction solution obtained in Example 16 and 0.5 ul of the reaction solution obtained in Example 3 in 25 μl of a reaction system.

Example 18

Incorporation of Fusion DNA of Lobster L21 Sequence, Melittin Signal Peptide, and Human NDST2 into Vector DNA (Procedures)

The fusion DNA obtained in Example 17 was used to collect plasmid DNA by the method shown in Example 5.

(Result)

A clone probably carrying the DNA fragment of interest was identified from *Escherichia coli* transformed with the ligation product. The nucleotide sequence of the DNA thereof was confirmed.

Example 19

Incorporation of Fusion DNA of Lobster L21 Sequence, Melittin Signal Peptide, and Human NDST2 into Baculovirus Genomic DNA (Procedures)

The DNA obtained in Example 18 was introduced into *Escherichia coli* DH10BAC (Invitrogen, U.S.A.), and DNA was collected by the method shown in Example 6.

Example 20

Introduction into *Spodoptera* frugiperda Cell, of Baculovirus Genomic DNA Incorporating Therein Fusion DNA of Lobster L21 Sequence, Melittin Signal Peptide, and Human NDST2

The DNA (baculovirus genomic DNA incorporating therein the lobster L21 sequence, melittin signal peptide, and human NDST2) obtained in Example 19 was used to prepare a baculovirus stock solution according to the method shown in Example 7.

Example 21

Acquisition of Serum Containing Anti-Human NDST2 Antibody

Peptide 1 (CLGRSKGRRYPDMD) (SEQ ID NO: 19) and Peptide 2 (CLREELQHSSLG) (SEQ ID NO: 20) in which a cysteine residue was added to the amino termini of the amino acid sequence at the 828th to 840th positions (LGRSKGR-RYPDMD) (SEQ ID NO: 17) and amino acid sequence at the 873rd to 883rd positions (LREELQHSSLG) (SEQ ID NO: 18) of human NDST2, respectively, were synthesized with a commercially available peptide synthesizer by an Fmoc method. 5 mg each of the obtained peptides was suspended in 4.5 ml of 100 mM sodium phosphate buffer solution (pH 7.2) and then covalently bonded with 0.5 ml of keyhole limpet hemocyanin (KLH) by stirring by rotation overnight at 4° C. by use of m-maleimidobenzoyl-N-hydroxy succinimide ester. Rabbits were immunized with the obtained KLH-peptide complexes by a method known in the art to obtain serum fractions.

Example 22

Preparation of Human NDST2 Peptide-Immobilized Column and Acquisition of Purified Anti-Human NDST2 Antibody Using the Column (Procedures)

The Peptides 1 and 2 dissolved in DMSO (dimethyl sulfoxide) were separately immobilized onto Epoxy-activated Sepharose 6B (Amersham Biosciences) according to the experimental procedures of the product to prepare peptide-immobilized resins. 0.4 ml each of the peptide-immobilized resins was equilibrated with TBS and then charged into chromatography column containers, and was mixed with 10 ml of serum obtained from the rabbit immunized with each peptide. The mixture was stirred by rotation overnight at 4° C. The chromatography column containers were mounted vertically and then washed sequentially with 10 ml of a Tris-HCl buffer solution (pH 7.5) containing 0.15 M NaCl, 20 ml of a Tris-HCl buffer solution (pH 7.5) containing 1 M NaCl and 1% Triton X-100, 20 ml of a Tris-HCl buffer solution (pH 7.5) containing 0.15 M NaCl, and 10 ml of 0.15 M NaCl, followed by elution with 1 ml of 0.1 M Glycine-HCl (pH 2.5). The eluted fractions were neutralized by the addition of 50 µl of 1 M Tris and used as solutions of purified anti-human NDST2 antibodies.

(Results)

The serum fraction of the rabbit immunized with the KLH-Peptide 1 complex was applied to the Peptide 1-immobilized column to obtain anti-hNDST2#1 as an eluted fraction. Likewise, anti-hNDST2#2 was obtained from the serum fraction of the rabbit immunized with the KLH-Peptide 2 complex.

Example 23

Figure 2:
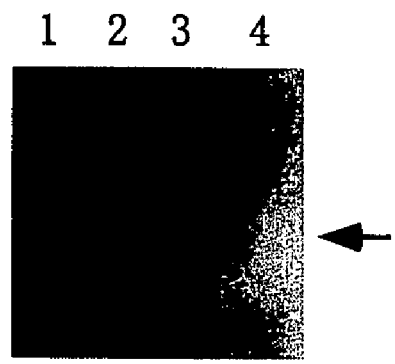
FIG. 2 shows a result of detecting human NDST2 in a *Spodoptera frugiperda* cell by using a purified anti-human NDST2 antibody.

Detection of Human NDST2 in *Spodoptera frugiperda* Cell Using Purified Anti-Human NDST2 Antibody The culture supernatant was mixed with 5×SDS-PAGE sample buffer having a ¼ volume thereof, then treated at 100° C. for 5 minutes, and subjected to 5% polyacrylamide electrophoresis. After the electrophoresis, the protein in the polyacrylamide gel was transferred to a PVDF membrane by a method known in the art. The membrane after transfer was shaken for 1 hour in 100 ml of a membrane washing solution (phosphate buffer solution containing 1% skimmed milk and 0.1% Tween-20). The membrane was shaken for 1 hour in 5 ml of a membrane washing solution containing 12.6 µg of the purified anti-human NDST2 antibody#1 or 16.6 µg of the purified anti-human NDST2 antibody#2 dissolved therein. The membrane was washed for 10 minutes three times with 100 ml of a membrane washing solution. The membrane was shaken for 1 hour in 5 ml of a membrane washing solution containing 0.4 µg of Horseradish Peroxidase-conjugated sheep anti-rabbit antibody dissolved therein. The membrane was washed for 10 minutes three times with 100 ml of a membrane washing solution. The membrane was incubated with a fluorescence emission reagent (e.g., Supersignal West Dura Substrate, Pierce, U.S.A.), and the fluorescence was then detected with an X-ray film.

hNDST2 was detected in the culture supernatant containing the virus stock solution by the method described above. First, the hNDST2 detection was performed in 1 µl of the culture supernatant (Lane 2) of Sf21 cells (serum-containing medium) infected with approximately 3 ml of the virus amplification solution derived from the vector of the fusion DNA of the lobster L21 sequence, gp67 signal peptide, and human NDST2. 1 µl of a culture supernatant (Lane 1) derived from pFastBac-1 was used as a control. Results of using the anti-hNDST2#1 and anti-hNDST2#2 are shown in FIGS. 1(A) and 1(B) below, respectively. The results shown in FIG. 1 demonstrated that the enzyme of interest in the culture supernatant can be detected by using either the anti-hNDST2#1 or the anti-hNDST2#2. Next, the hNDST2 detection was performed in 14 µl of the virus stock solution (Lane 2) derived from the vector of the fusion DNA of the lobster L21 sequence, gp67 signal peptide, and C-terminally 6×HIS tagged (SEQ ID NO: 21) human NDST2 and in 14 µl of the virus stock solution (Lane 1) derived from the vector of the fusion DNA of the lobster L21 sequence, melittin signal peptide, and human NDST2. 14 µl of the virus stock solution (Lane 3) derived from the vector of the fusion DNA of the lobster L21 sequence, gp67 signal peptide, and human NDST2 and 14 µl of a virus stock solution (Lane 4) derived from a cell comprising no vector DNA introduced therein were used as controls. Results using the anti-hNDST2#1 are shown in FIG. 2. The results shown in FIG. 2 demonstrated that the enzyme of interest can be detected in the virus stock solution derived from the vector of the fusion DNA of the lobster L21 sequence, gp67 signal peptide, and C-terminally 6×HIS tagged (SEQ ID NO: 21) human NDST2 and in the virus stock solution derived from the vector of the fusion DNA of the lobster L21 sequence, melittin signal peptide, and human NDST2, as in the virus stock solution derived from the vector of the fusion DNA of the lobster L21 sequence, gp67 signal peptide, and human NDST2.

INDUSTRIAL APPLICABILITY

The present invention has established a process of production of recombinant human N-deacetylase/N-sulfotransferase 2 from which the N-terminal sequence of the transmembrane domain has been removed, which comprises constructing a recombinant baculovirus expression vector comprising DNA encoding the 79th to 883rd amino acids of human N-deacetylase/N-sulfotransferase 2; transforming an insect cell with the expression vector; culturing the obtained transformant; and collecting an expression product secreted into the culture solution. The insect cell infected with the recombinant baculovirus expression vector of the present invention comprising DNA encoding the 79th to 883rd amino acids of human N-deacetylase/N-sulfotransferase 2 can highly express human N-deacetylase/N-sulfotransferase 2. The recombinant baculovirus expression vector of the present invention is an expression vector constructed so as to highly express human N-deacetylase/N-sulfotransferase 2.

The N-deacetylase/N-sulfotransferase 2 (NDST2) produced by the present invention, from which the N-terminal sequence of the transmembrane domain has been removed, is a soluble protein. The NDST2 has both N-deacetylase activity and N-sulfotransferase activity and as such, can be used in a variety of applications.

Specifically, NDST2 catalyzes the conversion reaction of acetyl groups to sulfate groups serving as the first step of modification reaction for the in-vivo biosynthesis of heparin/heparan sulfate from N-acetylheparosan. Therefore, soluble NDST2 easily obtained in large amounts by the present invention can be utilized for synthesizing heparin/heparan sulfate and analogous sugar chains (heparin-like sugar chains) thereof in large amounts by using as a raw material, N-acetylheparosan that can be produced with *Escherichia coli*. For example, N-sulfaminoheparosan, which itself is known to have anti-protease activity and anticoagulant activity, can be synthesized by allowing NDST2 to act on N-acetylheparosan. Furthermore, heparin/heparan sulfate and analogous sugar chains thereof can be synthesized by performing C5-epimerization, 2-O-sulfation, 6-O-sulfation, or 3-O-sulfation with epimerase, O-sulfotransferase, or the like. The heparin-like sugar chains can be utilized not only in pharmaceutical drugs and in antithrombotic treatment for medical equipment or devices, as in heparin/heparan sulfate, by utilizing their anticoagulant activity, but also for elucidating the functions of heparin/heparan sulfate-binding proteins (e.g., cell growth factors, cell adhesion factors, and blood coagulation-associated proteins) and diagnosing diseases associated with these proteins.

The invention claimed is:

1. A vector which comprises a signal peptide-encoding DNA that functions in a baculovirus expression vector, wherein the signal peptide is from baculovirus gp67, from silkworm bombyxin signal peptide, or bee melittin signal peptide; and
   a DNA ligated downstream of the signal peptide-encoding DNA, wherein the DNA encodes amino acids consisting of 79 to 883 of SEQ ID NO:2.

2. The vector according to claim 1 which further comprises a nontranslated leader sequence that promotes-expression of the DNA.

3. The vector according to claim 2 wherein the nontranslated leader sequence is lobster L21 DNA.

4. The vector according to claim 1 which further comprises a DNA encoding a histidine tag downstream of the DNA encoding the amino acids consisting of 79 to 883 of SEQ ID NO:2.

5. A recombinant baculovirus expression vector comprising
   baculovirus DNA,
   a DNA encoding a signal peptide positioned 3' to the baculovirus DNA, wherein the signal peptide functions in a baculovirus expression vector and is from baculovirus gp67, from silkworm bombyxin signal peptide, or bee melittin signal peptide; and
   a DNA, positioned 3' to the DNA encoding the signal peptide, encodes amino acids consisting of 79 to 883 of SEQ ID NO:2.

6. An insect cell which comprises the recombinant baculovirus expression vector of claim 5.

7. The insect cell of claim 6 which is *Spodoptera frugiperda* cell.

8. A process for producing human N-deacetylase/N-sulfotransferase 2, which comprises culturing the insect cell of claim 6 in a media under conditions to express and secrete human N-deacetylase/N-sulfotransferase 2.

9. The process of claim 8 wherein the insect cell is cultured in a serum-containing medium.

* * * * *